(12) United States Patent
Plumptre et al.

(10) Patent No.: US 10,576,210 B2
(45) Date of Patent: Mar. 3, 2020

(54) DRIVE MECHANISM FOR AN INJECTION DEVICE

(71) Applicant: SANOFI-AVENTIS DEUTSCHLAND GMBH, Frankfurt am Main (DE)

(72) Inventors: David Aubrey Plumptre, Worcestershire (GB); Robert Veasey, Worcestershire (GB); John David Cross, Northhampton (GB)

(73) Assignee: Sanofi-Aventis Deutschland GMBH, Frankfurt am Main (DE)

( * ) Notice: Subject to any disclaimer, the term of this patent is extended or adjusted under 35 U.S.C. 154(b) by 69 days.

(21) Appl. No.: 15/549,097

(22) PCT Filed: Feb. 10, 2016

(86) PCT No.: PCT/EP2016/052765
§ 371 (c)(1),
(2) Date: Aug. 4, 2017

(87) PCT Pub. No.: WO2016/128425
PCT Pub. Date: Aug. 18, 2016

(65) Prior Publication Data
US 2018/0028757 A1 Feb. 1, 2018

(30) Foreign Application Priority Data
Feb. 10, 2015 (EP) .................................... 15154488

(51) Int. Cl.
*A61M 5/315* (2006.01)

(52) U.S. Cl.
CPC .... *A61M 5/31535* (2013.01); *A61M 5/31551* (2013.01); *A61M 5/31575* (2013.01);
(Continued)

(58) Field of Classification Search
CPC .............. A61M 5/315; A61M 5/31551; A61M 5/31533; A61M 5/31536; A61M 5/31541; A61M 2005/3125
See application file for complete search history.

(56) References Cited

U.S. PATENT DOCUMENTS 6,004,297 A * 12/1999 Steenfeldt-Jensen ....................... A61M 5/31551 604/207
9,717,859 B2 * 8/2017 Harms ............... A61M 5/31543
(Continued)

FOREIGN PATENT DOCUMENTS

CN 102292120 12/2011
CN 103260677 8/2013
(Continued)

OTHER PUBLICATIONS

International Search Report and Written Opinion in International Application No. PCT/EP2016/052765, dated May 9, 2016, 12 pages.
International Preliminary Report on Patentability in International Application No. PCT/EP2016/052765, dated Aug. 15, 2017, 8 pages.

Primary Examiner — Bhisma Mehta
Assistant Examiner — Nidah M Hussain
(74) Attorney, Agent, or Firm — Fish & Richardson P.C.

(57) ABSTRACT

The present disclosure relates to a drive mechanism for an injection device for setting and dispensing of a dose of a medicament, the drive mechanism including
a tubular shaped housing component extending in an axial direction (z) and comprising an inner thread,
a tubular shaped display member having an outer thread engaged with the inner thread, and
a dose member axially displaceable between a dose setting position (S) and a dose dispensing position relative to the display member, (Continued)

wherein the display member includes at least one blocking member on its outer circumference to axially engage with a blocking structure on an inside facing sidewall portion of the housing component to block an axial displacement of the dose member from the dose setting position (S) towards the dose dispensing position.

19 Claims, 6 Drawing Sheets

(52) U.S. Cl.
CPC ..... *A61M 5/31585* (2013.01); *A61M 5/31541* (2013.01); *A61M 2205/581* (2013.01); *A61M 2205/582* (2013.01)

(56) References Cited

U.S. PATENT DOCUMENTS

2011/0319835 A1* 12/2011 Burren .............. A61M 5/31551
                                                            604/207
2013/0289518 A1   10/2013 Butler et al.

FOREIGN PATENT DOCUMENTS

| WO | WO 99/38554    | 8/1999 |
| WO | WO 2012/049138 | 4/2012 |
| WO | WO 2012/049139 | 4/2012 |
| WO | WO 2012/049140 | 4/2012 |
| WO | WO 2014/033197 | 3/2014 |

\* cited by examiner

DRIVE MECHANISM FOR AN INJECTION DEVICE

CROSS-REFERENCE TO RELATED APPLICATIONS

This application is a U.S. national stage application under 35 USC § 371 of International Application No. PCT/EP2016/052765, filed on Feb. 10, 2016, which claims priority to European Patent Application No. 15154488.9, filed on Feb. 10, 2015, the entire contents of which are incorporated herein by reference.

TECHNICAL FIELD

The present disclosure relates in one aspect to a drive mechanism for an injection device, such as a pen-type injector for setting and dispensing of a dose of a medicament. In particular, the disclosure relates to an injection device providing a minimum dose mechanism, i.e. a dose setting and dispensing mechanism that is only operable to dispense a dose if the dose exceeds a predefined minimum threshold.

BACKGROUND

Injection devices for setting and dispensing a single or multiple doses of a liquid medicament are as such well-known in the art. Generally, such devices have substantially a similar purpose as that of an ordinary syringe.

Injection devices, in particular pen-type injectors have to meet a number of user-specific requirements. For instance, with patient's suffering chronic diseases, such like diabetes, the patient may be physically infirm and may also have impaired vision. Suitable injection devices especially intended for home medication therefore need to be robust in construction and should be easy to use. Furthermore, manipulation and general handling of the device and its components should be intelligible and easy understandable. Moreover, a dose setting as well as a dose dispensing procedure must be easy to operate and has to be unambiguous.

Typically, such devices comprise a housing including in particular a cartridge holder, adapted to receive a cartridge at least partially filled with the medicament to be dispensed. Such devices further comprise a drive mechanism, usually having a displaceable piston rod which is adapted to operably engage with a piston of the cartridge. By means of the drive mechanism and its piston rod, the piston of the cartridge is displaceable in a distal direction or dispensing direction and may therefore expel a predefined amount of the medicament via a piercing assembly, which is to be releasably coupled with a distal end section of the housing of the injection device.

The medicament to be dispensed by the injection device is provided and contained in a multi-dose cartridge. Such cartridges typically comprise a vitreous barrel sealed in distal direction by means of a pierceable seal and being further sealed in proximal direction by the piston. With reusable injection devices an empty cartridge is replaceable by a new one. In contrast to that, injection devices of disposable type are to be discarded when the medicament in the cartridge has been dispensed or used-up.

Document EP 1 003 581 B1 discloses a drug delivery devices for selecting and dispensing a number of user variable doses of a medicament. This device includes a housing, a cartridge holder for retaining a cartridge containing the medicament, a piston rod displaceable relative to the cartridge holder and a dose setting mechanism.

For some applications it can be advantageous to limit the minimum medicament dose that can be delivered from a device as well as the maximum dose. This may, for example, ensure that only a therapeutically effective dose can be administered. Such a functionality may be particularly relevant to combinations of drugs, where a minimum quantity of the combined drug is required to ensure sufficient delivery of one element of the combination to be therapeutically effective, whilst allowing some variation of the dose, which may be important for the other element of the combination.

In some applications it may be advantageous to offer a device which allows delivery of only one fixed dose value but also permits a 'priming' operation to be undertaken before each dose is administered.

A further application could be for a therapy in which a range of discrete, non-sequential doses of a medication may be required. For example the range of doses may be needed to satisfy the therapeutic needs of different user groups, or to allow individual users to deliver a different dose at different times of the day e.g. in the morning or in the evening.

The present disclosure provides a drive mechanism for an injection device that provides a minimum dose function. The drive mechanism also provides a maximum dose function. The drive mechanism allows for a priming of the device, so that a user is able to dial and to deliver a rather small volume of medication, typically 2 international units (IU), to check whether flow occurs correctly through a needle assembly releasably attachable to a distal dispensing end of the device.

Implementation of the desired minimum and/or maximum dose function should be achievable by only modifying a limited number of existing device components. It is a further aim to individually modify minimum and maximum dose values or dose sizes by only changing a single or only a few components of the device. Hence, the minimum and/or maximum dose function of the device or its drive mechanism should be configurable by interchanging only one or a few components of the device or its drive mechanism. It is a further aim, that the improved drive mechanism is universally applicable to a large variety of drive mechanisms and injection devices. In particular, the improved drive mechanism should be equally applicable to disposable injection devices as well as to reusable injection devices.

SUMMARY

In one aspect the disclosure relates to a drive mechanism for an injection device operable to set and to dispense a dose of a medicament. In particular, the drive mechanism and the injection device are configured as a pen-type injector that provides setting of doses of variable size and subsequent dispensing thereof. The drive mechanism includes a tubular-shaped housing component extending in an axial direction (z). The housing component includes an inner thread, typically located at an inwardly facing sidewall portion. The thread is typically of helical type.

The drive mechanism further includes a tubular-shaped display member having an outer thread that is engaged with the inner thread. The display member is therefore located inside the housing component and is rotatable relative to the housing component in a dose incrementing direction, typically coinciding with a clockwise rotation and in a dose decrementing direction, typically coinciding with a counter-clockwise rotation relative to the housing component. Moreover, by dialing or rotating the display member in a dose incrementing direction, hence clockwise, the display member is subject to a helical, hence a combined rotational and translational motion relative to the housing component.

By turning clockwise the display member typically travels in a proximal axial direction. The display member has a helical sequence of items or numbers on its outer circumference that are arranged in accordance with the pitch of the threaded interface between housing component and display member. In this way, the items or numbers provided on an outer surface of the display member are visible through an aperture on a sidewall portion of the housing component.

The drive mechanism further includes a dose member axially displaceable between a dose setting position (S) and a dose dispensing position relative to the display member. Apart from the axial displacement between a proximal dose setting position and a distal dose dispensing position the dose member is axially constrained or axially coupled to the display member. The dose member is typically located in a proximal receptacle of the display member. The dose member is typically implemented as a dose button that is depressible in a distal direction for switching the drive mechanism from a dose setting mode into a dose dispensing mode.

The display member further includes at least one blocking member on its outer circumference to axially engage with a correspondingly-shaped blocking structure located on an inside facing sidewall portion of the housing component. The blocking structure is configured and designed to block an axial displacement of the dose member from the dose setting position (S) towards the dose dispensing position.

The blocking structure of the housing component is located in a predefined axial position and includes a predefined axial extension. Since the display member is subject to a helical motion relative to the housing component during dose setting the blocking member thereof is subject to a respective axial displacement. The blocking member and the display member could be subject to the same helical displacement. Hence, the blocking member could be an integral component or a portion of the display member. A blocking configuration is always obtained when the blocking member enters the region of the blocking structure. A blocking configuration is however released when the blocking member has passed the blocking structure. Hence, a blocking configuration and an inhibition to initiate a dose dispensing action is governed by the mutual engagement of blocking structure and blocking member. The axial position and axial extension of the blocking structure furthermore determines a minimum dose for a therapeutic application as well as a maximum dose for a priming procedure.

The blocking member may be in permanent axial engagement with the dose member either directly or indirectly, e.g. via a clutch sleeve or other components of the drive mechanism. When the blocking member engages with the blocking structure a distally directed displacement of the blocking member is not possible and hence impeded. Consequently and due to the direct or indirect axial abutment of blocking member and dose member also the dose member is blocked in its proximal dose setting position. Due to the axial abutment of the dose member with the blocking member and due to the blocking member's engagement with the blocking structure a distally directed displacement of the dose member is prevented.

When the blocking member and the blocking structure disengage due to a further axial displacement of the display member relative to the housing member the blocking member is released from the blocking structure and is no longer hindered to be displaced in an axial direction, typically in distal direction. Consequently, the dose member is then displaceable from the proximal dose setting position (S) in distal direction towards the dose dispensing position, thereby switching the drive mechanism from a dose setting mode into a dose dispensing mode.

According to another embodiment the blocking structure includes a blocking thread. The blocking thread is arranged at an inside facing sidewall portion of the housing component and includes the same pitch as the inner thread of the housing component. Since the blocking thread has the same pitch or lead as the inner thread, an axial engagement between the blocking member and the blocking structure is maintained as the blocking member travels through the axial zone, in which the blocking structure is located. Since blocking structure and inner thread have the same pitch, once engaged with the blocking structure the blocking member does not experience any further relative movement as it travels over the blocking thread.

In a further embodiment the blocking thread and the inner thread are axially separated. The blocking thread may be located near a distal portion of the tubular-shaped housing component while the inner thread may be located near a proximal portion of the housing component. It is furthermore conceivable, that blocking thread and inner thread are provided on different housing components that are mutually fixed. It is also conceivable that the inner thread is provided on an inside facing sidewall portion of a tubular-shaped insert axially and rotationally locked inside the tubular shaped housing component whereas the blocking thread is provided on an inside facing sidewall portion of a main housing component, hence of a proximal body of the housing of the drive mechanism or of the injection device.

Moreover, it is conceivable that the blocking thread and the inner thread are radially offset. Typically, the diameter of the inner thread may be slightly smaller than the radius of the blocking thread. In this way the outer thread of the display member is exclusively engageable with the inner thread of the housing component and the entire axial elongation of the display member can be provided with the outer thread in order to maximize an axial travel path for dose setting and dose dispensing, respectively.

Moreover, it is generally intended that the inner thread's axial extension is rather short and that the outer thread of the display member extends almost along the entire axial length of the display member. Accordingly, the blocking structure and hence the blocking thread may be located distally offset from the housing component's inner thread so as to selectively engage with the blocking structure provided at a distal end of the display member. In this way and due to the axial separation of blocking thread and inner thread the blocking member is configured to engage exclusively with the blocking structure but not with the inner thread of the housing component.

In a further embodiment the drive mechanism includes a clutch sleeve extending in axial direction and being axially positioned between the blocking member and the dose member. The clutch sleeve is typically axially located between the blocking member and the dose member. It serves as an axial thrust transfer means between the dose member and the blocking member. When the blocking member is in engagement with the blocking structure it is unable to flex or to move in distal axial direction. Any distally directed force applied to the dose member is transferred via the clutch sleeve directly onto the blocking member. Due to its axial engagement with the blocking structure the distally directed thrust exerted on the dose member is directly reacted by the blocking structure, thereby preventing a distally directed displacement of the dose member relative to the display member.

The clutch sleeve typically extends through the display member. It may be axially displaceable relative to the display member but may be permanently rotationally engaged with a piston rod of the drive mechanism, which piston rod typically includes a pressure piece or bearing at its distal end to axially engage and to distally abut against a proximal thrust receiving face of a piston of a cartridge. The clutch sleeve is typically permanently axially engaged and axially connected to the dose member. It may be axially biased relative to the display member by some kind of a spring means so that the display member and the clutch sleeve are displaceable from the proximal dose setting position towards the distal dose dispensing position against the action of a respective spring element.

According to a further embodiment the blocking member includes an inner protrusion extending radially inwardly from the display member to axially engage with the clutch sleeve. In this way, the clutch sleeve may axially abut with the blocking member's inner protrusion in order to establish an axial engagement between clutch sleeve and blocking member and hence between dose member and blocking member. It is even conceivable, that the inner protrusion of the blocking member is in permanent axial engagement with the clutch sleeve. Hence, the clutch sleeve is typically axially engaged with the display member at least when in dose setting mode. Then, a dose incrementing rotation of the dose member leading to a proximal displacement thereof relative to the housing component leads to a corresponding or identical axial displacement of the clutch sleeve.

However, for switching the drive mechanism from the dose setting mode into the dose dispensing mode the clutch sleeve is subject to at least a small but distinct axial displacement relative to the dose member, typically in the distal direction. Moreover, clutch sleeve and dose member may be selectively rotationally engageable by means of a clutch. If the clutch is open or released the display member is rotatable relative to the clutch sleeve. If the clutch is closed or engaged a rotation of the display member is equally transferred to a corresponding rotation of the clutch sleeve.

The inner protrusion of the blocking member is of particular benefit to axially engage with the clutch sleeve located inside the display member. By means of the radially inwardly extending inner protrusion an axial engagement with the clutch sleeve can be easily established, which clutch sleeve having a diameter smaller than the diameter of the display member and hence smaller than the diameter of the blocking member.

In a further embodiment the clutch sleeve is located inside the display member. The display member and clutch sleeve are typically arranged in a nested or convoluted way. The clutch sleeve may be completely enclosed by the surrounding display member. The clutch sleeve further includes a radially outwardly extending flange portion that is operable to axially engage with the radially inwardly extending inner protrusion of the blocking member. In this way, a radial extension of both, the inner protrusion and the flange portion of blocking member and clutch sleeve can be reduced to a minimum while still providing a sufficient radial overlap. The clutch sleeve's flange portion is typically provided at the clutch sleeve's distal end protruding distally from the distal end of the display member. Since the flange portion is configured for axial distal abutment with the blocking member, and in particular with the inner protrusion of the blocking member the blocking member or at least its inner protrusion is typically located distally from the clutch sleeve's flange portion.

Consequently and according to a further embodiment the blocking member arranged at a distal end of the display member further includes a flexible arm extending in a tangential and/or distal direction. The flexible arm is typically arc-shaped and coincides with the outer circumference of the tubular-shaped display member. When looking at the drive mechanism along the axial direction, the flexible arm is typically located completely inside the outer circumference of the display member. The flexible arm may comprise a helical structure and may therefore extend distally from the distal end of the display member. The flexible arm typically includes a bottom portion that is connected to or integrally formed with the display member. The flexible arm includes a free end which is located at an axial distance from the distal end of the tubular-shaped display member.

Typically, the blocking member and hence its flexible arm is integrally formed with the display member, so that providing the blocking member only requires modification to an existing display member. Implementation and assembly of an additional component to establish the blocking or minimum dose mechanism is therefore not required. In this way, the implementation of the minimum dose function is rather cost efficient in terms of component manufacturing and device assembly.

Providing a flexible arm is of particular benefit for keeping the blocking member in permanent axial engagement with the dose member, in particular via the clutch sleeve. In this way a rather direct and definite blocking feedback can be given to a user when the blocking function is active. The direct and permanent axial engagement of the clutch sleeve with the blocking member and the dose member provides a robust and direct haptic feedback to a user almost free of slack. When in a release configuration the blocking member and hence its flexible arm is free to flex in distal direction, thereby allowing the dose member and/or the clutch sleeve to be displaced in distal direction accordingly for switching from the dose setting mode to the dose dispensing mode.

In a further embodiment the blocking member includes an outer protrusion extending radially outwardly from the display member to axially engage with the blocking structure. By means of the outer protrusion the blocking member may axially engage with the blocking structure of the housing component while the blocking member with its inner protrusion axially engages with the dose member, typically via the axially extending clutch sleeve. It is of particular benefit when both, inner protrusion and outer protrusion are located or arranged at or near the free end of the flexible arm. In this way a load path to block a distally directed displacement of the dose member does not travel through the flexible arm but traverses only the free end thereof, which is axially sandwiched between the blocking structure and the dose member, in particular between the blocking thread of the blocking structure and the radially outwardly extending flange portion of the clutch sleeve being in permanent axial abutment or axial engagement with the dose member.

According to a further embodiment the outer protrusion includes a radially outwardly facing edge frictionally engaging with the blocking structure or with the inside facing sidewall portion of the housing. The flexible arm, in particular its free end may not only be deflectable or flexible in axial direction but also in radial direction. It is particularly intended that the outer protrusion even displaces radially outwardly when a blocking situation arises so as to frictionally engage with the blocking structure or with the inside facing sidewall portion of the housing component.

This friction is of particular benefit since any axial and distally directed load acting on the dose member and eventually also acting on the display member may tend to rotate the display member in a dose decrementing direction. By means of the radially outwardly facing edge of the outer protrusion frictionally engaging with the blocking structure or with the inside facing sidewall portion the robustness and mechanical stability of the blocking configuration can be even improved.

According to a further embodiment the blocking structure includes a proximally facing proximal edge that is inwardly inclined in proximal direction to engage with a correspondingly inclined distal edge of the outer protrusion of the blocking member. These mutually corresponding inclined proximal and distal edges of blocking structure and outer protrusion serve to displace and to urge the outer protrusion of the blocking member radially outwardly to frictionally engage with the blocking structure or with the inside facing sidewall portion of the housing component.

According to a further embodiment the axial position of a distal end of the blocking structure on the housing component defines a maximum size of a dose for a priming procedure. As long as the blocking member is located distally from the distal end of the blocking structure it is free to be flexed or to be displaced in distal direction as a consequence of the dose member being depressed in distal direction for dose dispensing. If a priming capability, i.e. setting of a small dose and subsequent test delivery thereof should be provided, the axial position of the distal end of the blocking structure is arranged at an axial position of the housing component that coincides with the blocking member when a dose larger than, for example, 2 international units (IU) or 3 IU is set.

If a user rotates the dose member further in a dose incrementing direction the blocking member thereof engages with the housing component's blocking structure so that the blocking member, in particular its outer protrusion axially abuts with and slides along the blocking structure. The distal end of the blocking structure may be provided with a chamfer so that the blocking member experiences a kind of a proximally directed pre-tension or flexing as it engages with the blocking thread. As the display member along with the blocking member is dialed further in the dose incrementing direction the blocking member remains flexed in the distal direction against a proximal side edge of the blocking structure, hence its blocking thread.

The axial position of the proximal end of the blocking structure typically defines a minimum size of a therapeutic dose that may be set and subsequently dispensed by the drive mechanism. It is only when blocking member and blocking structure disengage, which disengagement coincides with the predefined minimum dose, that the blocking member, hence its flexible arm is flexible or displaceable in distal direction under the effect of the dose member and/or the clutch sleeve.

In another embodiment the drive mechanism further includes a piston rod to axially engage with a piston of a cartridge. The piston rod includes an outer thread engaged with an inner thread of a housing component. The housing component may be configured as a further insert to be fixed inside the main housing or body of the injection device. It is also conceivable that the housing component which is threadedly engaged with the piston rod is integrally formed with the main housing or body of the drive mechanism or injection device. The drive mechanism further includes a drive sleeve that is permanently rotationally locked to the piston rod and which is exclusively rotatable in a dose decrementing direction, e.g. counter-clockwise relative to the housing component via a one-way ratchet.

By means of the one-way ratchet the drive sleeve is blocked to rotate in a dose incrementing direction relative to the housing. In this way it is guaranteed that the piston rod can only travel in the distal direction but never in the opposite proximal direction. The rotational interlock of the drive sleeve and the piston rod may be obtained via a spline interface. Hence, the piston rod may comprise a longitudinal groove engaged with a radially inwardly extending protrusion of the drive sleeve. Apart from that the drive sleeve almost completely encloses the piston rod, at least when the drive mechanism is in an initial configuration. The drive sleeve is also axially fixed to the housing but is free to rotate relative to the housing. The piston rod experiences a distally directed translational displacement because the drive sleeve rotates during a dispense operation and since the drive sleeve is axially fixed or axially constrained to the housing.

In a further embodiment the clutch sleeve is permanently rotationally locked to the drive sleeve located inside the clutch sleeve. The drive sleeve may be further in splined engagement with the clutch sleeve. The splined engagement of drive sleeve and clutch sleeve may be of permanent type so that the clutch sleeve is free to be axially displaced relative to the drive sleeve, thereby still maintaining a rotational interlock between drive sleeve and clutch sleeve. Irrespective of a mutual axial position or distance of clutch sleeve and drive sleeve a dose decrementing rotation of the clutch sleeve is equally transferable to the drive sleeve in order to advance the piston rod in distal direction. Due to its permanent rotational interlock and rotational engagement with the drive sleeve and the one-way ratchet to the drive sleeve also the clutch sleeve is only rotatable in a dose decrementing direction but never in a dose incrementing direction.

According to a further embodiment the clutch sleeve is located inside the display member. The clutch sleeve in axial abutment with the dose member is further axially biased in proximal direction relative to the display member. By means of the axial bias the clutch between the clutch sleeve and the display member is kept open or released so that the display member is free to rotate relative to the clutch sleeve during dose setting. By means of the axial bias a kind of a flexible or force sensitive axial coupling between the display member and the dose member is provided by way of which the dose member is dragged or pushed in the proximal direction by the display member when the display member is subject to a dose incrementing rotation relative to the housing component during a dose setting procedure.

The clutch sleeve and the display member are selectively rotationally lockable by means of a clutch. The clutch is engageable by a displacement of the clutch sleeve in a distal dose dispensing direction relative to the display member. Typically, the clutch includes a radially outwardly extending flange portion towards its proximal end featuring a distally facing toothed structure to engage with a correspondingly shaped proximally facing toothed structure of the display member. By displacing the clutch sleeve in distal direction relative to the display member the clutch engages and a dose decrementing rotation inducible by the display member equally transfers to the clutch sleeve. Due to the splined engagement of clutch sleeve and drive sleeve also the drive sleeve starts to rotate in the dose decrementing direction thereby inducing a corresponding rotation of the piston rod due to a further splined engagement therewith. Because of the threaded engagement of the piston rod with the housing component the piston rod becomes subject to a distally directed advancing motion.

The clutch between the clutch sleeve and the display member is further operable to transfer distally directed thrust exerted on a dose member and transferred to the dial clicker member towards the display member. As the display member is subject to a distally directed thrust it starts to rotate due to the helical path and the rather large pitch of its threaded engagement with the housing component.

In another aspect the disclosure further relates to an injection device for setting and dispensing of a dose of a medicament. The injection device includes a housing to accommodate a drive mechanism as described above and further includes a cartridge arranged inside the housing. The injection device actually accommodates the drive mechanism. The drive mechanism is assembled inside the housing. It is operably engageable with the cartridge or it may be already operably engaged with the cartridge upon a final assembly of the injection device. The housing may comprise a proximal body and a distally located cartridge holder, wherein the body is configured to accommodate the drive mechanism, hence all mechanically interacting components of the device while the cartridge holder is configured to receive at least a distal portion of the cartridge that is filled with a liquid medicament to be dispensed by means of the injection device and its drive mechanism.

In the present context, the distal direction points in the direction of the dispensing and of the device, where, preferably a needle assembly is provided having a double-tipped injection needle, one end of which is to be inserted into biological tissue or into the skin of a patient for delivery of the medicament and the other end of which is inserted into the cartridge that contains the medicament.

The proximal end or proximal direction denotes the end of the device or a component thereof, which is furthest away from the dispensing end. Typically, an actuating member is located at the proximal end of the injection device, which is directly operable by a user to be rotated for setting of a dose and which is operable to be depressed in distal direction for dispensing of a dose.

The term "drug" or "medicament", as used herein, means a pharmaceutical formulation containing at least one pharmaceutically active compound, wherein in one embodiment the pharmaceutically active compound has a molecular weight up to 1500 Da and/or is a peptide, a protein, a polysaccharide, a vaccine, a DNA, a RNA, an enzyme, an antibody or a fragment thereof, a hormone or an oligonucleotide, or a mixture of the above-mentioned pharmaceutically active compound, wherein in a further embodiment the pharmaceutically active compound is useful for the treatment and/or prophylaxis of diabetes mellitus or complications associated with diabetes mellitus such as diabetic retinopathy, thromboembolism disorders such as deep vein or pulmonary thromboembolism, acute coronary syndrome (ACS), angina, myocardial infarction, cancer, macular degeneration, inflammation, hay fever, atherosclerosis and/or rheumatoid arthritis, wherein in a further embodiment the pharmaceutically active compound includes at least one peptide for the treatment and/or prophylaxis of diabetes mellitus or complications associated with diabetes mellitus such as diabetic retinopathy, wherein in a further embodiment the pharmaceutically active compound includes at least one human insulin or a human insulin analogue or derivative, glucagon-like peptide (GLP-1) or an analogue or derivative thereof, or exendin-3 or exendin-4 or an analogue or derivative of exendin-3 or exendin-4.

Insulin analogues are for example Gly(A21), Arg(B31), Arg(B32) human insulin; Lys(B3), Glu(B29) human insulin; Lys(B28), Pro(B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin and Des(B30) human insulin.

Insulin derivatives are for example B29-N-myristoyl-des (B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N—(N-palmitoyl-Y-glutamyl)-des(B30) human insulin; B29-N—(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

Exendin-4 for example means Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH2.

Exendin-4 derivatives are for example selected from the following list of compounds:

H-(Lys)4-des Pro36, des Pro37 Exendin-4(1-39)-NH2,
H-(Lys)5-des Pro36, des Pro37 Exendin-4(1-39)-NH2,
des Pro36 Exendin-4(1-39),
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39); or
des Pro36 [Asp28] Exendin-4(1-39),
des Pro36 [IsoAsp28] Exendin-4(1-39),
des Pro36 [Met(O)14, Asp28] Exendin-4(1-39),
des Pro36 [Met(O)14, IsoAsp28] Exendin-4(1-39),
des Pro36 [Trp(O2)25, Asp28] Exendin-4(1-39),
des Pro36 [Trp(O2)25, IsoAsp28] Exendin-4(1-39),
des Pro36 [Met(O)14 Trp(O2)25, Asp28] Exendin-4(1-39),
des Pro36 [Met(O)14 Trp(O2)25, IsoAsp28] Exendin-4 (1-39), wherein the group -Lys6-NH2 may be bound to the C-terminus of the Exendin-4 derivative;

or an Exendin-4 derivative of the sequence
des Pro36 Exendin-4(1-39)-Lys6-NH2 (AVE0010),
H-(Lys)6-des Pro36 [Asp28] Exendin-4(1-39)-Lys6-NH2,
des Asp28 Pro36, Pro37, Pro38Exendin-4(1-39)-NH2,
H-(Lys)6-des Pro36, Pro38 [Asp28] Exendin-4(1-39)-NH2,
H-Asn-(Glu)5des Pro36, Pro37, Pro38 [Asp28] Exendin-4(1-39)-NH2,
des Pro36, Pro37, Pro38 [Asp28] Exendin-4(1-39)-(Lys)6-NH2,
H-(Lys)6-des Pro36, Pro37, Pro38 [Asp28] Exendin-4(1-39)-(Lys)6-NH2, H-Asn-(Glu)5-des Pro36, Pro37, Pro38 [Asp28] Exendin-4(1-39)-(Lys)6-NH2, H-(Lys)6-des Pro36 [Trp(O2)25, Asp28] Exendin-4(1-39)-Lys6-NH2, H-des Asp28 Pro36, Pro37, Pro38 [Trp(O2)25] Exendin-4(1-39)-NH2, H-(Lys)6-des Pro36, Pro37, Pro38 [Trp(O2)25, Asp28] Exendin-4(1-39)-NH2, H-Asn-(Glu)5-des Pro36, Pro37, Pro38 [Trp(O2)25, Asp28] Exendin-4(1-39)-NH2, des Pro36, Pro37, Pro38 [Trp(O2)25, Asp28] Exendin-4(1-39)-(Lys)6-NH2, H-(Lys)6-des Pro36, Pro37, Pro38 [Trp(O2)25, Asp28] Exendin-4(1-39)-(Lys)6-NH2, H-Asn-(Glu)5-des Pro36, Pro37, Pro38 [Trp(O2)25, Asp28] Exendin-4(1-39)-(Lys)6-NH2, H-(Lys)6-des Pro36 [Met(O)14, Asp28] Exendin-4(1-39)-Lys6-NH2, des Met(O)14 Asp28 Pro36, Pro37, Pro38 Exendin-4(1-39)-NH2, H-(Lys)6-desPro36, Pro37, Pro38 [Met(O)14, Asp28] Exendin-4(1-39)-NH2, H-Asn-(Glu)5-des Pro36, Pro37, Pro38 [Met(O)14, Asp28] Exendin-4(1-39)-NH2, des Pro36, Pro37, Pro38 [Met(O)14, Asp28] Exendin-4(1-39)-(Lys)6-NH2, H-(Lys)6-des Pro36, Pro37, Pro38 [Met(O)14, Asp28] Exendin-4(1-39)-(Lys)6-NH2, H-Asn-(Glu)5 des Pro36, Pro37, Pro38 [Met(O)14, Asp28] Exendin-4(1-39)-(Lys)6-NH2, H-Lys6-des Pro36 [Met(O)14, Trp(O2)25, Asp28] Exendin-4(1-39)-Lys6-NH2, H-des Asp28 Pro36, Pro37, Pro38 [Met(O)14, Trp(O2)25] Exendin-4(1-39)-NH2, H-(Lys)6-des Pro36, Pro37, Pro38 [Met(O)14, Asp28] Exendin-4(1-39)-NH2, H-Asn-(Glu)5-des Pro36, Pro37, Pro38 [Met(O)14, Trp(O2)25, Asp28] Exendin-4(1-39)-NH2, des Pro36, Pro37, Pro38 [Met(O)14, Trp(O2)25, Asp28] Exendin-4(1-39)-(Lys)6-NH2, H-(Lys)6-des Pro36, Pro37, Pro38 [Met(O)14, Trp(O2)25, Asp28] Exendin-4(S1-39)-(Lys)6-NH2, H-Asn-(Glu)5-des Pro36, Pro37, Pro38 [Met(O)14, Trp(O2)25, Asp28] Exendin-4(1-39)-(Lys)6-NH2;

or a pharmaceutically acceptable salt or solvate of any one of the afore-mentioned Exendin-4 derivative.

Hormones are for example hypophysis hormones or hypothalamus hormones or regulatory active peptides and their antagonists as listed in Rote Liste, ed. 2008, Chapter 50, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

A polysaccharide is for example a glucosaminoglycane, a hyaluronic acid, a heparin, a low molecular weight heparin or an ultra low molecular weight heparin or a derivative thereof, or a sulphated, e.g. a poly-sulphated form of the above-mentioned polysaccharides, and/or a pharmaceutically acceptable salt thereof. An example of a pharmaceutically acceptable salt of a poly-sulphated low molecular weight heparin is enoxaparin sodium.

Antibodies are globular plasma proteins (~150 kDa) that are also known as immunoglobulins which share a basic structure. As they have sugar chains added to amino acid residues, they are glycoproteins. The basic functional unit of each antibody is an immunoglobulin (Ig) monomer (containing only one Ig unit); secreted antibodies can also be dimeric with two Ig units as with IgA, tetrameric with four Ig units like teleost fish IgM, or pentameric with five Ig units, like mammalian IgM.

The Ig monomer is a "Y"-shaped molecule that consists of four polypeptide chains; two identical heavy chains and two identical light chains connected by disulfide bonds between cysteine residues. Each heavy chain is about 440 amino acids long; each light chain is about 220 amino acids long. Heavy and light chains each contain intrachain disulfide bonds which stabilize their folding. Each chain is composed of structural domains called Ig domains. These domains contain about 70-110 amino acids and are classified into different categories (for example, variable or V, and constant or C) according to their size and function. They have a characteristic immunoglobulin fold in which two β sheets create a "sandwich" shape, held together by interactions between conserved cysteines and other charged amino acids.

There are five types of mammalian Ig heavy chain denoted by α, δ, ε, γ, and μ. The type of heavy chain present defines the isotype of antibody; these chains are found in IgA, IgD, IgE, IgG, and IgM antibodies, respectively.

Distinct heavy chains differ in size and composition; α and γ contain approximately 450 amino acids and δ approximately 500 amino acids, while μ and ε have approximately 550 amino acids. Each heavy chain has two regions, the constant region ($C_H$) and the variable region ($V_H$). In one species, the constant region is essentially identical in all antibodies of the same isotype, but differs in antibodies of different isotypes. Heavy chains γ, α and δ have a constant region composed of three tandem Ig domains, and a hinge region for added flexibility; heavy chains μ and ε have a constant region composed of four immunoglobulin domains. The variable region of the heavy chain differs in antibodies produced by different B cells, but is the same for all antibodies produced by a single B cell or B cell clone. The variable region of each heavy chain is approximately 110 amino acids long and is composed of a single Ig domain.

In mammals, there are two types of immunoglobulin light chain denoted by λ and κ. A light chain has two successive domains: one constant domain (CL) and one variable domain (VL). The approximate length of a light chain is 211 to 217 amino acids. Each antibody contains two light chains that are always identical; only one type of light chain, κ or λ, is present per antibody in mammals.

Although the general structure of all antibodies is very similar, the unique property of a given antibody is determined by the variable (V) regions, as detailed above. More specifically, variable loops, three each the light (VL) and three on the heavy (VH) chain, are responsible for binding to the antigen, i.e. for its antigen specificity. These loops are referred to as the Complementarity Determining Regions (CDRs). Because CDRs from both VH and VL domains contribute to the antigen-binding site, it is the combination of the heavy and the light chains, and not either alone, that determines the final antigen specificity.

An "antibody fragment" contains at least one antigen binding fragment as defined above, and exhibits essentially the same function and specificity as the complete antibody of which the fragment is derived from. Limited proteolytic digestion with papain cleaves the Ig prototype into three fragments. Two identical amino terminal fragments, each containing one entire L chain and about half an H chain, are the antigen binding fragments (Fab). The third fragment, similar in size but containing the carboxyl terminal half of both heavy chains with their interchain disulfide bond, is the crystalizable fragment (Fc). The Fc contains carbohydrates, complement-binding, and FcR-binding sites. Limited pepsin digestion yields a single F(ab')2 fragment containing both Fab pieces and the hinge region, including the H—H interchain disulfide bond. F(ab')2 is divalent for antigen binding. The disulfide bond of F(ab')2 may be cleaved in order to obtain Fab'. Moreover, the variable regions of the heavy and light chains can be fused together to form a single chain variable fragment (scFv).

Pharmaceutically acceptable salts are for example acid addition salts and basic salts. Acid addition salts are e.g. HCl or HBr salts. Basic salts are e.g. salts having a cation selected from alkali or alkaline, e.g. Na+, or K+, or Ca2+, or an ammonium ion N+(R1)(R2)(R3)(R4), wherein R1 to R4 independently of each other mean: hydrogen, an optionally substituted C1-C6-alkyl group, an optionally substituted C2-C6-alkenyl group, an optionally substituted C6-C10-aryl group, or an optionally substituted C6-C10-heteroaryl group. Further examples of pharmaceutically acceptable salts are described in "Remington's Pharmaceutical Sciences" 17. ed. Alfonso R. Gennaro (Ed.), Mark Publishing Company, Easton, Pa., U.S.A., 1985 and in Encyclopedia of Pharmaceutical Technology.

Pharmaceutically acceptable solvates are for example hydrates.

It will be further apparent to those skilled in the art that various modifications and variations can be made to the present invention without departing from the spirit and scope of the invention. Further, it is to be noted, that any reference numerals used in the appended claims are not to be construed as limiting the scope of the invention.

BRIEF DESCRIPTION OF THE FIGURES

In the following, embodiments of the drive mechanism and the injection device are described in detail by making reference to the figures, in which.

DETAILED DESCRIPTION

Figure 1:
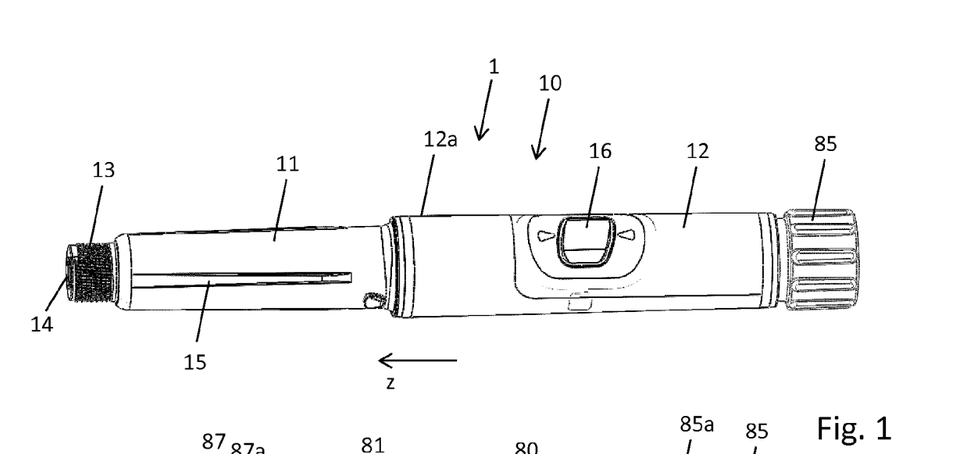
FIG. 1 shows a schematic side view of the injection device.
Figure 4:
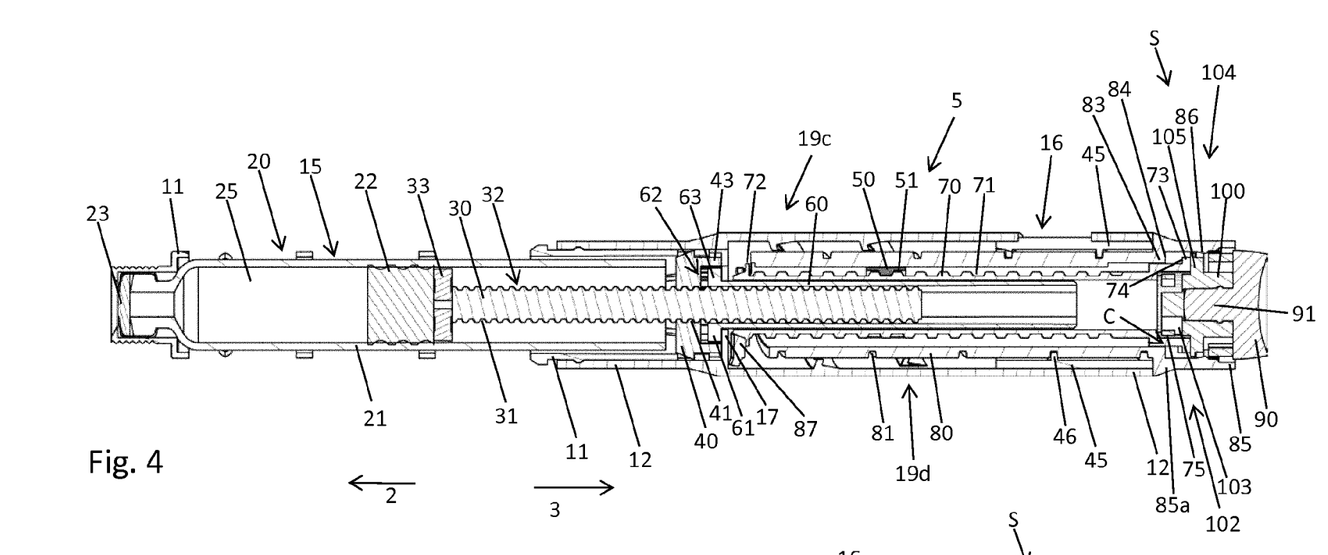
FIG. 4 is a longitudinal cross section through the entire injection device.

The injection device 1 as shown in FIGS. 1 and 4 includes a housing 10 of elongated shape and extending in an axial direction (z). The housing includes a distal end facing in distal direction 2 and a proximal end facing in proximal direction 3. The housing 10 includes a cartridge holder 11 forming a distal end of the housing and further includes a body 12 forming a proximal component of the housing. Both, the cartridge holder 11 and the body are of substantially tubular shape. The diameter of the cartridge holder 11 is slightly smaller than the diameter of the body 12 so that a proximal end of the cartridge holder 11 is received in a distal receptacle of the body 12.

Figure 5:
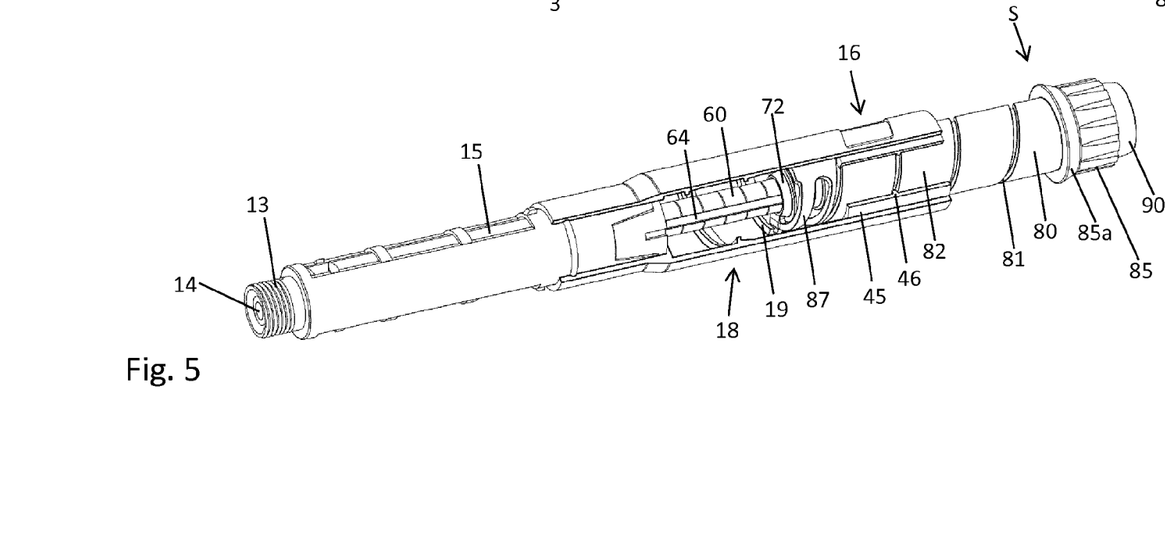
FIG. 5 is a partially cut view of various components of the drive mechanism in a perspective view.

The injection device 1 may be configured as a disposable device, wherein the cartridge holder 11 is non-releasably attached to the body 12 and wherein a drive mechanism 5 accommodated inside the body 12 does not provide a reset function. In alternative embodiments the injection device 1 may be configured as a reusable device, wherein the cartridge holder 11 is releasably attached to the body 12, thus allowing replacement of an empty cartridge and allowing to reset the drive mechanism 5. The cartridge holder 11 as illustrated in FIGS. 4 and 5 includes at least one aperture in its sidewall providing an inspection window 15 that supports visual inspection of the content of a cartridge 20 located therein.

At its distal end the cartridge holder 11 includes a socket 13, which is typically threaded and which is configured to releasably engage with a piercing assembly, in particular with a hub of a piercing assembly further comprising a double-tipped injection needle. A proximal end of the tipped injection needle is insertable through a distal through opening 14 of the cartridge holder 11 so as to pierce a distal seal 23 of the cartridge 20 and to gain access to the medicament 25 located in the inner volume or interior of the barrel 21 of the cartridge 20. The cartridge 20, in particular its barrel is typically made of an inert material. Typically, the cartridge barrel 21 is made of a vitreous material, such as glass.

The proximal end of the cartridge 20 is sealed by a rubber piston 22 that is displaceable in distal direction 2 under the effect of a distally advancing piston rod 30. The piston rod 30 extends in the axial direction and includes an outer thread 31 threadedly engaged with an inner thread 41 of an insert 40 that is rigidly attached and rigidly fixed inside the body 12. The distal end of the piston rod 30 is further provided with a pressure piece or bearing 33 that is rotatable relative to the piston rod 30. Due to its threaded engagement with the insert 40 the piston rod 30 is subject to an axial displacement when rotated during a dose dispensing action. In order to limit friction with the piston 22 the bearing 33 is typically in non-rotative abutment with a proximal thrust receiving face of the piston 22 while the rotating piston rod 30 exerts distally directed pressure to the piston 22 via the bearing 33.

The piston rod 30 is rotationally locked to a drive sleeve 60, which in an initial configuration of the device 1 almost completely encloses the piston rod 30. The drive sleeve 60 is typically splined with the piston rod 30 so as to transfer a driving torque from the drive sleeve 60 to the piston rod 30. For this purpose the piston rod 30 includes at least one or even several elongated grooves 32 that are in permanent engagement with a radially inwardly extending protrusion 66 extending radially inwardly from an inner sidewall portion of the drive sleeve 60. By means of a splined engagement between drive sleeve 60 and piston rod 30 the piston rod 30 is able to advance distally while the drive sleeve 60 is axially fixed in or relative to the body 12. At all times the drive sleeve 60 remains rotationally locked to the piston rod 30 in order to transfer a driving torque from the drive sleeve 60 towards the piston rod 30.

The drive sleeve 60 further includes a radially outwardly extending flange 61 at its distal end. By way of the flange 61 the drive sleeve 60 is axially fixed between the insert 40 and a radially inwardly extending protrusion 17 of the body 12. Moreover, at a radially outwardly extending side edge the flange 61 includes a pawl 63 to engage with a correspondingly shaped toothed structure 43 of the insert 40. The toothed structure 43 is facing radially inwardly at an inward facing sidewall portion of the insert 40. The toothed structure 43 and the pawl or several pawls 63 form a one-way ratchet 62 that prevents and inhibits a dose incrementing or clockwise rotation of the drive sleeve 60 relative to the housing 10. Hence, during dose setting the drive sleeve 60 is rotationally fixed relative to the body 12. In this way also the piston rod 30 is secured against rotation as long as the drive mechanism 5 is in a dose setting mode.

During dose dispensing the one-way ratchet 62 allows a dose decrementing rotation of the drive sleeve 60 and hence of the piston rod 30 relative to the body 12. During dose dispensing and during a decrementing rotation, e.g. counterclockwise the one way ratchet generates an audible and/or tactile feedback indicating to a user of the device 1 that a dose dispensing procedure is in progress. Every time a pawl 63 of the drive sleeve 60 ratchets over a tooth of the toothed structure 43 a distinct click sound is generated, wherein the generation of subsequent click sounds may correspond and coincide with a distinct number of units of the dose actually dispensed.

Figure 6:
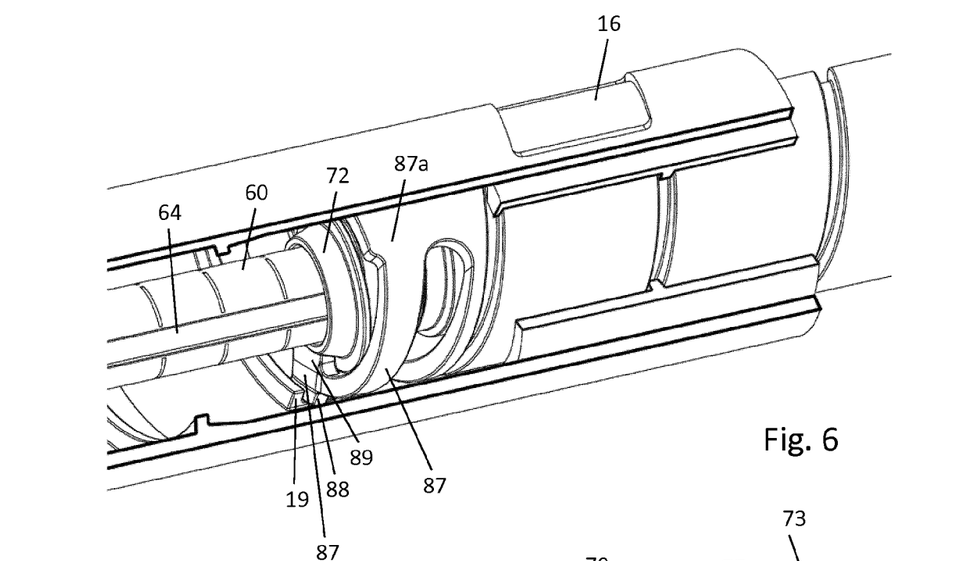
FIG. 6 is an enlarged view of a portion of the drive mechanism where the blocking member is in blocking configuration.
Figure 7:
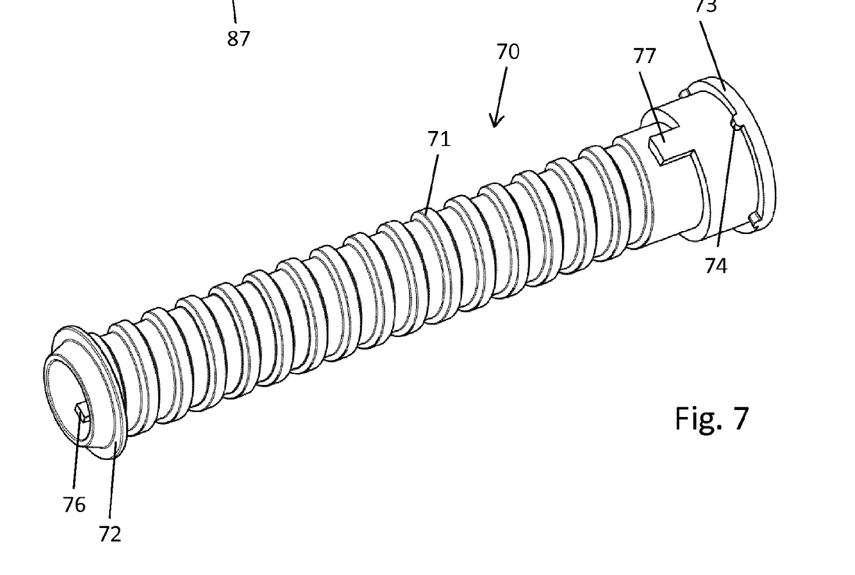
FIG. 7 shows an isolated perspective view of the clutch sleeve.

The drive mechanism 5 further includes a clutch sleeve 70 enclosing the drive sleeve 60 and being in splined engagement with the drive sleeve 60. The clutch sleeve 70 as illustrated in FIG. 7 includes a radially inwardly extending protrusion 76 on an inside facing sidewall portion that engages and matches with a longitudinal groove 64 of the drive sleeve 60 as illustrated in FIG. 6. In this way the clutch sleeve 70 is free to be axially moved relative to the drive sleeve 60 while staying in rotational engagement therewith.

On its outer circumference the clutch sleeve 70 includes a thread 71 that is in threaded engagement with a corresponding thread 51 of a last dose member 50. The last dose member 50 further includes a radially outwardly extending protrusion 52 that is splined with an inside facing sidewall portion of a tubular-shaped display member 80. In this way the last dose member 50 is in permanent rotational engagement with the display member 80 and therefore rotates together with the display member 80 as the display member 80 is subject to a rotation relative to the clutch sleeve 70. This is typically the case as long as the drive mechanism is in a dose setting mode. In dose dispensing mode the display member 80 and the clutch sleeve 70 rotate together since they are rotationally coupled via a clutch C. Then, the last dose member 50 remains stationary relative to the clutch sleeve 70 and also to the display member 80. Only at the start of a dispense operation there is a limited axial movement between the last dose member 50 and the display member 80 because the clutch sleeve is moved axially relative to the display member when depressed distally.

In dose setting mode however, in which the clutch sleeve 70 is rotationally locked to the body 12 the last dose member is subject to a proximally directed translation. The last dose member 50, in particular its axial position on the clutch sleeve 70 therefore reflects and corresponds to the amount of medicament 25 left in the cartridge 20. Assuming that only very little amount of the medicament 25 is left in the cartridge 20 the last dose member 50 is located rather close to a stop 77 at a proximal end of the threaded portion 71 of the clutch sleeve 70.

Assuming that a user intends to set a dose exceeding the amount of medicament 25 left in the cartridge 20 the last dose member 50 engages with the last dose stop 77. Typically, the last dose member 50 includes an axially extending stop 53 with an axially extending stop face to get in direct and tangential abutment with a respective stop face of the last dose stop 77. Dialing of a dose exceeding the amount of medicament 25 left in the cartridge 20 is therefore effectively blocked and prevented.

The clutch sleeve 70 further includes a radially outwardly extending flange portion 72 near its distal end, which flange portion has a larger diameter than the diameter of the axially adjacent thread 71. The flange portion 72 is configured to provide a minimum dose function of the drive mechanism 5 as will be explained below.

Figure 8:
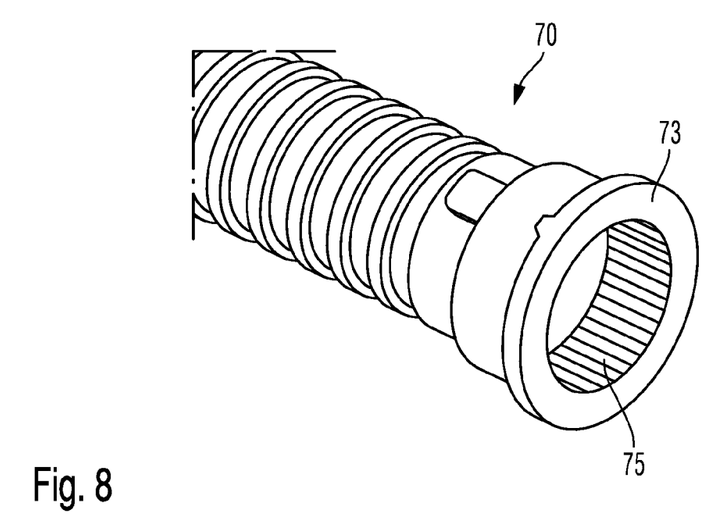
FIG. 8 is a perspective view of the proximal end of the clutch sleeve.
Figure 9:
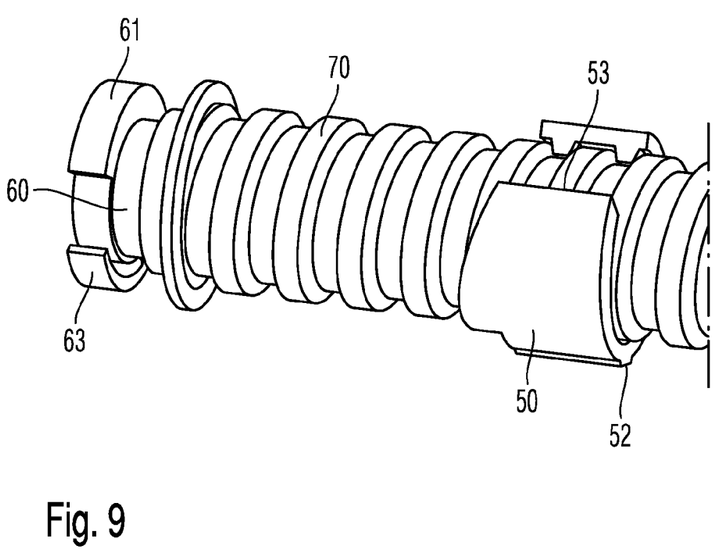
FIG. 9 is an isolated perspective view of the assembly of clutch sleeve, last dose member and blocking member.

The clutch sleeve 70 further includes a radially outwardly extending flange portion 73 at its proximal end having a toothed structure 74 facing in distal direction. In addition, and as shown in FIG. 8, the clutch sleeve includes a toothed structure 75 at an inside facing sidewall portion of a proximal receptacle.

Figure 2:
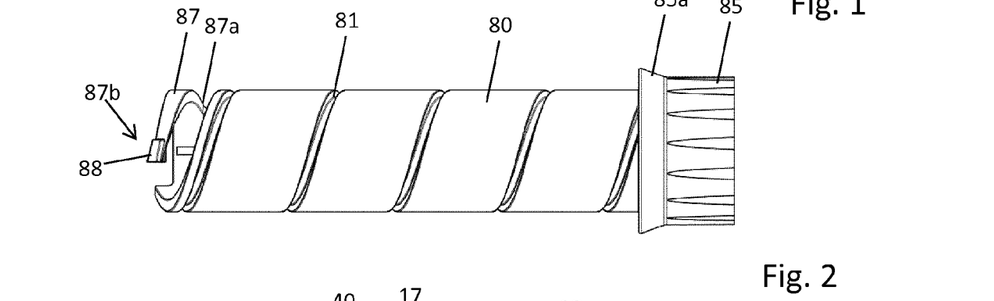
FIG. 2 shows an isolated side view of the display member with the blocking member at its distal end.

The drive mechanism 5 further includes a display member 80 of sleeve like shape as shown in detail in FIG. 2. The tubular shaped display member 80 includes an outer thread 81 that is in engagement with a corresponding thread 46 of a proximal insert 45. The proximal insert 45 is located near the proximal end of the body 12; it is fixed inside the body 12. As shown in FIG. 4, the insert 45 extends across an aperture of the body 12 thereby forming a dose indicating window. Typically, at least in the region coinciding with the aperture in a sidewall 12a of the body 12 the insert 45 is substantially transparent. It is even conceivable that the insert includes a magnifying lens in order to improve legibility of numbers printed on the outer circumference of the sleeve of the display member 80.

As it is apparent from FIG. 4, the display member 80 is in permanent threaded engagement with the insert 45 and hence with the body 12. Near its proximal end the display member 80 includes a dial portion 85 or a skirt 85a which skirt actually abuts with a proximal end of the body 12 when the drive mechanism 5 is in a zero dose configuration initially or at the end of a dose dispensing procedure. The axial abutment of the skirt 85a and the body 12 prevents dialing of a dose less than 0. Moreover, this abutment serves as a zero dose stop to terminate a dispensing action of the injection device 1. Alternatively, a respective zero dose stop could be also provided directly on the distal end of the display member 80.

The dial portion 85 is hollow as shown in FIG. 4. Its outer circumference includes a gripping surface by way of which a user may easily dial a dose of the medicament by turning the dial portion 85 in a dose incrementing direction, e.g. clockwise. Consequently, the display member 80 is translated in proximal direction out of the body 12 following a helical path in accordance to the threaded engagement of display member 80 and insert 45. When dialing or setting a dose, increasing and consecutive numbers provided on the outer circumference of the display member 80 show up in the window 16.

Hence, the display member 80 includes an information surface 82 on its outer circumference, which information surface 82 follows a helical path in accordance to the structure of the thread 81. The information surface 82 is helically wound axially between the thread 81.

The proximal end of the dial portion 85 of the display member 80 is closed by a dose member 90, acting as a dose button. The dose member 90 includes a stem 91 that is axially fixed to a dial clicker member 100 that is located inside the tubular-shaped dial portion 85. The dial clicker member 100 is axially engaged and axially fixed to the dose member 90. It is axially sandwiched between the proximal end of the clutch sleeve 70 and the radially outwardly extending dose button portion of the dose member 90.

The dial clicker member 100 includes and forms two separate one-way ratchets. A one-way ratchet 102 is established between the dial clicker member 100 and the clutch sleeve 70. A further one-way ratchet 104 is formed between the dial clicker member 100 and the display member 80. The one-way ratchet 102 is formed by at least one radially outwardly extending pawl 103 of the dial clicker member 100 engaging with radially inwardly facing teeth 75 of the clutch sleeve 70. The other one-way ratchet 104 is formed by at least one radially outwardly biased pawl 105 engaging with a toothed structure 86 on an inside facing sidewall portion of the dial portion 85 of the display member 80.

The two one-way ratchets 102, 104 are geometrically opposite. During dose setting, hence during a dose increasing rotation of the display member 80 relative to the rotationally fixed clutch sleeve 70 the ratchet 104 generates a click sound, thereby indicating that an increasing number of discreet doses is actually dialed and set. Hence, the ratchet 104 allows a dose incrementing rotation of the display member 80 relative to the dial clicker member 100 while the other ratchet 102 inhibits and blocks a rotation of the dial clicker member 100 in dose incrementing direction relative to the clutch sleeve. Hence, during a dose incrementing dialing of the display member 80, the dial clicker member 100 is rotationally fixed through the ratchet 102 while the other ratchet 104 generates an audible and/or tactile click sound.

In the event that a dose actually set is too high, the ratchet 104 rotationally locks the display member 80 to the dial clicker member 100. When the display member 80 is rotated in dose decrementing direction, e.g. counterclockwise the dial clicker member 100 follows this rotation. Then, the ratchet 102 generates an audible click sound as it meshes with its pawl 103 along the toothed structure 75 of the clutch sleeve 70. In this context it is to be mentioned, that the mechanical resistance of the ratchet 102 is substantially smaller than the mechanical resistance to overhaul the one-way ratchet 62. In this way it is effectively prevented, that a dose decrementing rotation of the display member 80 transfers any dose decrementing torque to the drive sleeve 60 and hence to the piston rod 30.

The clutch sleeve 70 and the display member 80 are selectively engageable via a clutch C. The clutch is formed by a distally facing toothed structure 74 of the proximal flange 73 of the clutch sleeve 70 and a correspondingly-shaped toothed structure 84 facing in proximal direction and being located at a radially inwardly stepped portion of the inside facing sidewall of the display member 80. In the illustration according to FIG. 4, showing the drive mechanism 5 in the dose setting mode S the clutch C is open or disengaged since the mutually corresponding toothed structures 74, 84 are axially separated.

In this configuration the display member 80 is rotatable relative to the body 12 while the drive sleeve 60 and clutch sleeve 70 are rotationally fixed to the body 12. Typically, the clutch C is kept in the disengaged state by some kind of a biasing feature, such like a spring element or spring feature acting between the display member 80 and the clutch sleeve 70. The clutch sleeve 70 is typically biased in proximal direction relative to the display member 80 to keep the clutch C disengaged during dose setting. Moreover and alternatively, also the spring element 70 could serve and act as the blocking member.

In the following section, setting of a dose is described.

For setting of a dose, a user takes the body 12 and starts to dial the display member 80 by means of the dial portion 85 in a dose incrementing direction, hence clockwise. Due to the threaded engagement of the display member 80 and the insert 45 or the body 12 the display member 80 is subject to a proximally directed translation relative to the body 12 while consecutive increasing numbers on the information surface 82 of the display member 80 show up in the window 16 of the body 12. Due to the axial bias between display member 80 and clutch sleeve 70 the clutch sleeve 70 is also subject to a distally directed displacement.

Since the clutch sleeve 70, in particular its proximal flange portion 73 is in axial abutment with the dial clicker member 100 also the dial clicker member 100 and the dose member 90 are equally subject to a proximally directed displacement relative to the body 12. Consequently, the display member 80, the clutch sleeve 70 as well as the dose member 90 extend in proximal direction 3 from the body 12 and further separate from the proximal end of the body 12 as the size of the dose is increased.

A dose incrementing rotation of the display member 80 is stopped when a maximum settable dose is reached. For this the insert 45 and the display member 80 may comprise mutually engaging stop features by way of which a further dose incrementing rotation of the display member relative to the body 12 is stopped. During the dose setting and hence during a dose increasing rotation of the display member 80 the clutch sleeve 70 and the drive sleeve 60 as well as the piston rod 30 do not rotate. This is due to the one-way ratchet 62 by way of which the drive sleeve 60 is actually prevented to rotate in dose incrementing direction. Since the drive sleeve 60 and the clutch sleeve 70 are in splined engagement also the clutch sleeve 70 is prevented from rotating in a dose incrementing direction. Due to the splined engagement between drive sleeve 60 and clutch sleeve 70 the clutch sleeve 70 is however free to axially move relative to the drive sleeve 60 and to extend out of the body 12 as a dose size is further increased.

When dialing a dose the display member 80 rotates relative to the clutch sleeve 70. Since the last dose member 50 is splined with the display member 80 and since the last dose member 50 is threadedly engaged with the clutch sleeve 70 it is subject to a proximally directed displacement as the display member 80 is rotated in dose incrementing direction.

In the following dispensing of a dose is described.

Once a dose of desired size has been set, a dispensing procedure is simply initiated by depressing the dose member 90 in distal direction 2 thereby advancing the dial clicker member 100 as well as the clutch sleeve 70 simultaneously in the distal direction 2. The dose member 90 travels axially, but because it is in contact with the users finer or thumb does not rotate, whilst the clutch sleeve 70 and the display member rotate in unison in a dose decrementing direction, e.g. counterclockwise.

For this to happen the clutch C between the clutch sleeve 70 and the display member 80 is closed. This is achieved due to the distally directed displacement of the clutch sleeve 70, thereby engaging the mutually corresponding toothed structures 74, 84. Moreover, since the clutch C also transfers a distally directed thrust from the dose member 90 towards the clutch sleeve 70 also the display member 80 experiences a distally directed thrust, which due to the pitch of the threaded engagement of display member 80 and insert 45 leads to a dose decrementing rotation of the display member 80 relative to the body 12. Since the clutch sleeve 70 and the display member 80 are rotationally locked via the clutch C also the clutch sleeve 70 rotates in dose decrementing direction in unison with the display member 80.

Consequently since display member 80 and clutch sleeve 70 rotate together the last dose member 50 remains axially stationary with respect to the clutch sleeve 70 and the display member 80. Due to the splined engagement of the clutch sleeve 70 and the drive sleeve 60 also the drive sleeve 60 becomes subject to a dose decrementing rotation, which rotation is equally transferred to the piston rod 30 via the splined engagement of drive sleeve 60 and piston rod 30. Consequently the one-way ratchet 62 of the drive sleeve 60 generates repeated click sounds indicating that a dose dispensing action is actually in progress.

Due to the splined engagement of drive sleeve 60 and piston rod 30 the piston rod 30 rotates in dose decrementing direction, e.g. counterclockwise. Due to its threaded engagement with the insert 40 the piston rod 30 experiences a distally directed advancing motion thereby exerting distally directed thrust to the piston 22. Consequently, the piston 22 is urged in distal direction 2 for a predefined distance, thereby expelling a predefined amount of the liquid medicament 25 from the cartridge 20 through the needle assembly intersecting the distal seal 23.

In order to implement a minimum dose function there is provided a blocking member 87 at the distal end of the display member 80 and a blocking structure 18, presently in the form of a blocking thread 19 at an inside facing sidewall portion 12a of the body 12. Furthermore the insert 45 is axially offset from the blocking thread 19 with its radially inward facing thread 46. The blocking member 87 as shown in FIG. 2 includes an arc-shaped arm having a base portion 87a by way of which the blocking member 87 is unitarily formed or connected to the distal end of the tubular-shaped display member 80.

The blocking member 87 includes a free end section 87b that is located at an axial distance, hence distally from the distal end of the display member 80. The free end section 87b of the blocking member 87 is flexible in axial direction (z). Moreover and as it is best seen in FIG. 6 the arc-shaped blocking arm or blocking member 87 includes an inner protrusion 89 that is in axial abutment with a distally facing portion of the clutch sleeve's 70 flange portion 72. The free end section 87b further includes an outer protrusion 88 radially outwardly extending from the blocking member 87 to axially engage with the blocking thread 19.

In particular, the proximal face of the radially inwardly extending inner protrusion 89 axially engages with the distal face of the flange portion 72 whereas the outer protrusion 88, in particular its distally facing surface axially engages with a proximal edge 19a of the blocking thread 19. The blocking thread 19 has the same lead as the threaded engagement between display member 80 and insert 45. Once the display member 80 is rotated to such an extent that corresponds to a dose that is greater than the maximum priming dose and smaller than the prescribed minimum dose the blocking member 87, in particular its free end section 87b engages with the proximally facing edge 19a of the blocking thread 19 as illustrated in FIG. 3.

Figure 3:
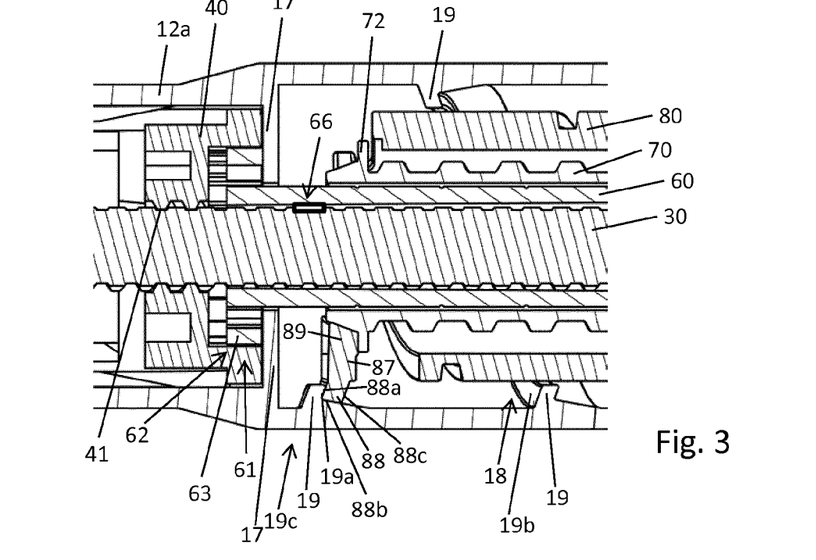
FIG. 3 is an enlarged cross section through a portion of the injection device in the region of the blocking member.

Since the blocking member 87 with its inner protrusion 89 is also in axial abutment with the clutch sleeve 70 this engagement configuration as shown in FIG. 3 is operable to inhibit any distally directed displacement of the clutch sleeve 70 and all further components of the drive mechanism in axial abutment therewith. Consequently, the blocking configuration as shown in FIG. 3 is operable to inhibit and to block a distally directed displacement of the dose member 90. Moreover, since the dose member 90 is permanently axially engaged with the clutch sleeve 70, either directly or via the dial clicker member 100, a distally directed thrust or force acting on the dose member 90 is immediately blocked and reacted by the axial engagement of the blocking member 87 with the blocking thread 19.

It is of particular benefit, that inner and outer protrusions 89, 88 of the free end section 87b of the blocking member 87 are located at the same tangential position of the blocking member 87. As seen in radial direction and as shown in FIG. 3, the inner protrusion 89 is just radially opposite the outer protrusion 88. In this way, a load path between the clutch sleeve 70 and its flange portion 72 with the blocking thread 19 is comparatively short.

As it is further illustrated in detail in FIG. 3 the blocking thread 19 of the blocking structure 18 features a proximally facing proximal edge 19a that is inwardly inclined in proximal direction 2. Correspondingly, also a distal edge 88a of the outer protrusion 88 is correspondingly inclined so as to match with the proximally facing edge 19a of the blocking thread. Due to these inclined and mutually engaging edges 19a, 88a the blocking member 87, in particular its free end section 87b is driven radially outwardly as the free end section 87 is subject to a distally directed thrust or force transferred via the clutch sleeve 70. Due to the shape of the inclined edges 19a, 88a the free end section 87 is further flexed and urged radially outwardly so that a radially outwardly facing radial edge 88b of the outer protrusion 88 frictionally engages with an inside facing portion of the sidewall 12a of the body 12. In this way the blocking provided by the blocking member 87 can even be improved and enhanced.

The distal end 19c of the blocking thread 19 determines a maximum dose for a priming procedure. While a proximal end 19d of the blocking thread 19 determines a minimum dose that is dispensable by means of the injection device 1. It is furthermore conceivable that for instance the distal end 19c of the blocking thread 19 is chamfered so that upon engagement of the blocking member 87 with the blocking thread 19 the blocking member 87, in particular its free end section 87b experiences a small but distinct proximal displacement leading to a flexing of the blocking member 87. In this way, the blocking member 87 may be at least slightly flexed in proximal direction so that it slides along and in contact with the proximal edge 19a of the blocking thread 19 as the display member 80 is further dialed in dose incrementing direction.

Figure 10:
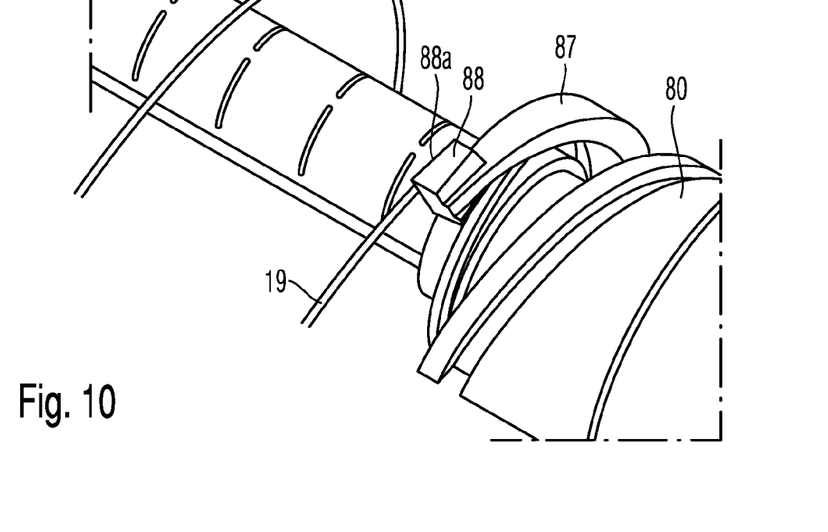
FIG. 10 is a perspective and artificial view of the blocking member engaged with the proximal end of the blocking structure.

A configuration slightly below the minimum dispensable dose size is indicated in FIG. 10. As shown there, the distal facing distal edge 88a of the blocking member's 87 outer protrusion 88 axially abuts in distal direction against the proximally facing proximal edge 19a of the blocking thread 19. Simultaneously, also the flange portion 72 of the clutch sleeve 70 is in axial abutment with the proximally facing edge of the inner protrusion 89. In this configuration distally directed displacement of the clutch sleeve 70 is blocked by the free end section 87b of the blocking member 87 being axially sandwiched or axially squeezed between clutch sleeve 70 and blocking structure 18 of the body 12.

Figure 11:
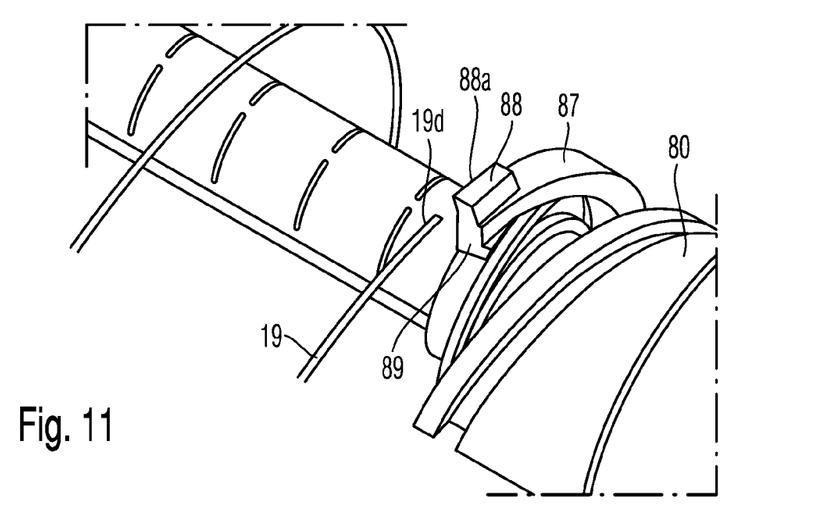
FIG. 11 shows a configuration, in which the blocking member is located proximally from the proximal end of the blocking structure.
Figure 12:
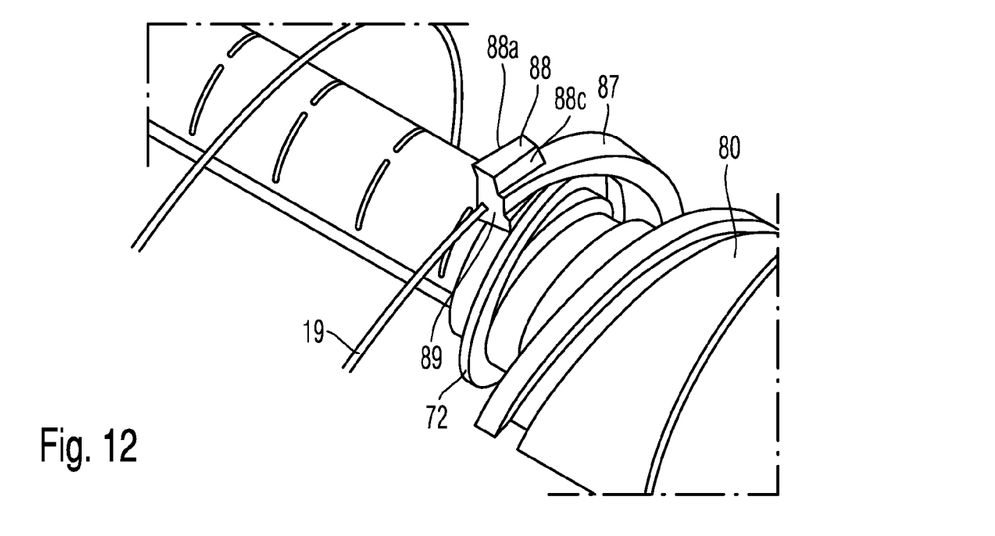
FIG. 12 shows a configuration in which the blocking member deflects past the proximal end of the blocking structure during dose dispensing and FIG. 13 shows a configuration in which the blocking structure slides along a distally facing edge of a blocking structure or blocking thread when a dose dispensing has been interrupted at a dose size being smaller than the predefined minimum dose size.
Figure 13:
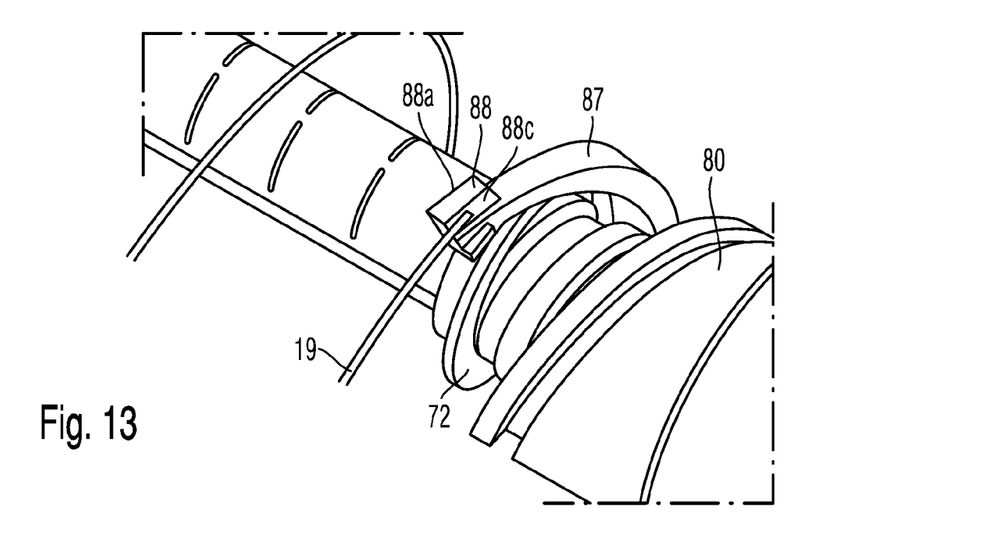

As the display member 80 is dialed a bit further in the dose incrementing direction the blocking member 87 disengages from the blocking structure 19 and is then free to flex in the distal direction 2 as a distally directed thrust is applied to the clutch sleeve 70. During dose dispensing the dose member 90 is kept in a depressed state, in which also the clutch sleeve 70 with its distal flange portion 72 protrudes a bit further from the distal end of the display member 80. As can be seen in FIG. 12 in comparison to FIG. 11 the free end section 87b of the blocking member 87 is slightly flexed and urged in distal direction 2 compared to the tubular portion of the display member 80.

Consequently, also the relative position between the blocking member 87 and the proximal end 19d of the blocking thread 19 changes. Consequently, the proximally facing edge 88c of the outer protrusion 88 is located distally from the distal edge 19b of the blocking thread 19. As the device 1 is subject to a dose dispensing procedure during which the display member 80 rotates in a dose decrementing direction, e.g. counterclockwise, the blocking member 87 is located at the distal edge 19b of the blocking thread 19. In the event that a dose dispensing procedure is interrupted at a dose size to be delivered that is less than the predefined minimum dose, hence when the blocking member 87 is axially overlapping with the blocking structure 18 the clutch sleeve 70 returns into its initial proximal state, thereby no longer flexing the blocking member 87 in distal direction.

As a consequence, the blocking member 87 may relax in proximal direction, whereby the proximal edge 88c of the outer protrusion 88 axially engages with the distally facing distal edge 19b of the blocking thread 19. In this configuration a further dispensing procedure can be resumed at any time since the blocking member 87 is located distally from the blocking structure 18 or blocking thread 19. A distally directed flexing or a displacement of the blocking member's free end section 87 is possible. Consequently, the clutch sleeve 70 and the dose member are displaceable in distal direction 2 to close and to engage the clutch C and to continue with the interrupted dose dispensing procedure. In this way and according to a patient's preferences a comparatively large dose can be subsequently injected at two different sites.

LIST OF REFERENCE NUMERALS 1 injection device
2 distal direction
3 proximal direction
5 drive mechanism
10 housing
11 cartridge holder
12 body
12a sidewall
13 socket
14 through opening
15 inspection window
16 window
17 protrusion
18 blocking structure
19 blocking thread
19a proximal edge
19b distal edge
19c distal end
19d proximal end
10 cartridge
21 barrel
22 piston
23 seal
24 cap
25 medicament
30 piston rod
31 thread
32 groove
33 bearing
40 insert
41 thread
43 toothed structure
45 insert
46 thread
50 last dose member
51 thread
52 protrusion
53 stop
60 drive sleeve
61 flange
62 ratchet
63 pawl
64 groove
66 protrusion
70 clutch sleeve
71 thread
72 flange portion
73 flange portion
74 toothed structure
75 toothed structure
76 protrusion
77 stop
80 display member
81 thread
82 information surface
83 flange
84 toothed structure
85 dial portion
85a skirt
86 toothed structure
87 blocking member
87a base portion
87b free end section
88 outer protrusion
88a distal edge
88b radial edge
88c proximal edge
90 inner protrusion
91 dose member
91 stem
100 dial clicker member
102 ratchet
103 pawl
104 ratchet
105 pawl

The invention claimed is:

1. A drive mechanism for an injection device configured to set and dispense a dose of a medicament, the drive mechanism comprising:
a tubular shaped housing component extending in an axial direction and comprising an inner thread;
a tubular shaped display member having an outer thread engaged with the inner thread; and
a dose member axially displaceable from a proximal dose setting position to a distal dose dispensing position relative to the display member to initiate dispensing of the dose of the medicament,
wherein the display member comprises at least one blocking member on an outer circumference of the display member, the at least one blocking member configured to axially engage with a blocking structure on an inside facing sidewall portion of the housing component to block an axial displacement of the dose member from the proximal dose setting position towards the distal dose dispensing position.

2. The drive mechanism according to claim 1, wherein the blocking structure comprises a blocking thread, and wherein the blocking thread and the inner thread have the same pitch.

3. The drive mechanism according to claim 2, wherein the blocking thread and the inner thread are axially separated.

4. The drive mechanism according to claim 1, further comprising a clutch sleeve extending in the axial direction and being axially positioned between the at least one blocking member and the dose member.

5. The drive mechanism according to claim 4, wherein the at least one blocking member comprises an inner protrusion extending radially inwardly from the display member to axially engage with the clutch sleeve.

6. The drive mechanism according to claim 4, wherein the clutch sleeve is located inside the display member and has a radially outwardly extending flange portion at a distal end of the clutch sleeve protruding distally from the display member.

7. The drive mechanism according to claim 1, wherein the at least one blocking member is arranged at a distal end of the display member and comprises a flexible arm extending in a tangential direction and a distal direction.

8. The drive mechanism according to claim 1, wherein the at least one blocking member is arranged at a distal end of the display member and comprises a flexible arm extending in a tangential direction or a distal direction.

9. The drive mechanism according to claim 1, wherein the at least one blocking member comprises an outer protrusion extending radially outwardly from the display member to axially engage with the blocking structure.

10. The drive mechanism according to claim 9, wherein the outer protrusion comprises a radially outwardly facing edge frictionally engaging with the blocking structure or with the inside facing sidewall portion.

11. The drive mechanism according to claim 9, wherein the blocking structure comprises a proximally facing proximal edge inwardly inclined in a proximal direction to engage with a correspondingly inclined distal edge of the outer protrusion.

12. The drive mechanism according to claim 1, wherein an axial position of a distal end of the blocking structure on the housing component defines a maximum size of a dose for a priming procedure and wherein an axial position of a proximal end of the blocking structure on the housing component defines a minimum size of a therapeutic dose for injection.

13. The drive mechanism according to claim 1, further comprising:
a piston rod configured to axially engage with a piston of a cartridge, wherein the piston rod comprises an outer thread engaged with an inner thread of a second housing component; and
a drive sleeve permanently rotationally locked to the piston rod and being exclusively rotatable in a dose decrementing direction relative to the second housing component via a one-way ratchet.

14. The drive mechanism according to claim 13, further comprising a clutch sleeve, wherein the clutch sleeve is permanently rotationally locked to the drive sleeve located inside the clutch sleeve, and wherein the clutch sleeve is axially displaceable relative to the drive sleeve.

15. The drive mechanism according to claim 13, further comprising a clutch sleeve, wherein the clutch sleeve is located inside the display member, wherein the clutch sleeve in axial abutment with the dose member is axially biased in a proximal direction relative to the display member, and wherein the clutch sleeve and the display member are selectively rotationally lockable by a clutch, wherein the clutch is engageable by a displacement of the clutch sleeve in a distal direction relative to the display member.

16. The drive mechanism according to claim 1,
wherein the at least one blocking member is axially engageable with the dose member, and
wherein when the at least one blocking member is axially engaged with the blocking structure, the at least one blocking member is configured to impede a distally directed displacement of the dose member from the proximal dose setting position towards the distal dose dispensing position.

17. An injection device configured to set and dispense a dose of a medicament, the injection device comprising:
a housing accommodating a drive mechanism, the drive mechanism comprising:
a tubular shaped housing component extending in an axial direction and comprising an inner thread;
a tubular shaped display member having an outer thread engaged with the inner thread; and
a dose member axially displaceable from a proximal dose setting position to a distal dose dispensing position relative to the display member to initiate dispensing of the dose of the medicament,
wherein the display member comprises at least one blocking member on its outer circumference to axially engage with a blocking structure on an inside facing sidewall portion of the housing component to block an axial displacement of the dose member from the proximal dose setting position towards the distal dose dispensing position; and
a cartridge arranged inside the housing and filled with a liquid medicament.

18. The injection device according to claim 17, wherein the medicament comprises a pharmaceutically active compound.

19. The injection device according to claim 17,
wherein the at least one blocking member is axially engageable with the dose member,
wherein when the at least one blocking member is axially engaged with the blocking structure, the at least one blocking member is configured to impede a distally directed displacement of the dose member from the proximal dose setting position towards the distal dose dispensing position.

* * * * *